(12) United States Patent
Cumberlidge et al.

(10) Patent No.: US 8,653,036 B2
(45) Date of Patent: Feb. 18, 2014

(54) METHODS OF TREATING RETINITIS PIGMENTOSA

(75) Inventors: Garth Cumberlidge, Gloucester, MA (US); Horacio U. Saragovi, Montreal (CA); Karen Meerovitch, Cote Saint-Luc (CA)

(73) Assignee: Mimetogen Pharmaceuticals Inc. (CA)

( * ) Notice: Subject to any disclaimer, the term of this patent is extended or adjusted under 35 U.S.C. 154(b) by 0 days.

(21) Appl. No.: 13/203,293

(22) PCT Filed: Feb. 26, 2010

(86) PCT No.: PCT/US2010/025575
§ 371 (c)(1),
(2), (4) Date: Mar. 16, 2012

(87) PCT Pub. No.: WO2010/099436
PCT Pub. Date: Sep. 2, 2010

(65) Prior Publication Data
US 2012/0165271 A1    Jun. 28, 2012

Related U.S. Application Data

(60) Provisional application No. 61/208,806, filed on Feb. 27, 2009.

(51) Int. Cl.
*A61K 38/00*    (2006.01)
*A61P 9/10*    (2006.01)
*A61P 27/02*    (2006.01)

(52) U.S. Cl.
USPC ..................................................... 514/20.8

(58) Field of Classification Search
None
See application file for complete search history.

(56) References Cited

U.S. PATENT DOCUMENTS

2003/0211982 A1    11/2003    Saragovi et al.
2009/0318335 A1    12/2009    Vitagliano et al.

FOREIGN PATENT DOCUMENTS

| WO | 2008056217 A1 | 5/2008 |
| WO | WO 2008/070132 A2 | 6/2008 |
| WO | WO 2008/076904 A1 | 6/2008 |
| WO | WO 2008/104000 A2 | 8/2008 |
| WO | WO 2008149244 A2 * | 12/2008 |

OTHER PUBLICATIONS

Colangelo, A.M., A New Nerve Growth Factor—Mimetic Peptide Active on Neuropathic Pain in Rats, 2008, J. of Neuroscience, 28(11):2698-2709.
Zaccaro, M. C., et al., "Selective Small Molecule Peptidomimetic Ligands of TrkC and TrkA Receptors Afford Discrete or Complete Neurotrophic Activities," *Chemistry & Biology*, vol. 12, pp. 1015-1028 (2005).
Lebrun-Julien, F., et al., "Inhibition of $p75^{NTR}$ in Glia Potentiates TrkA-Mediated Survival of Injured Retinal Ganglion Cells," *Molecular and Cellular Neuroscience*, vol. 40, pp. 410-420 (2009).
Lenzi, L., et al., "Effect of Exogenous Administration of Nerve Growth Factor in the Retina of Rats with Inherited Retinitis Pigmentosa," *Vision Research*, vol. 45, pp. 1491-1500 (2005).
Notification of Transmittal of the International Search Report and the Written Opinion of the International Searching Authority, or the Declaration, for International Application No. PCT/US2010/025575, mailed on Aug. 12, 2010, consisting of 15 pages.

* cited by examiner

*Primary Examiner* — Marcela M Cordero Garcia
*Assistant Examiner* — Kaipeen Yang
(74) *Attorney, Agent, or Firm* — Pillsbury Winthrop Shaw Pittman LLP

(57) ABSTRACT

The present invention relates to methods of treating retinitis pigmentosa using β-turn peptidomimetic cyclic compounds or derivatives thereof. The β-turn peptidomimetic cyclic compounds can be used alone, in combination and/or in conjunction with one or more other compounds, molecules or drugs useful in treating retinitis pigmentosa.

8 Claims, 2 Drawing Sheets

FIG 1A.
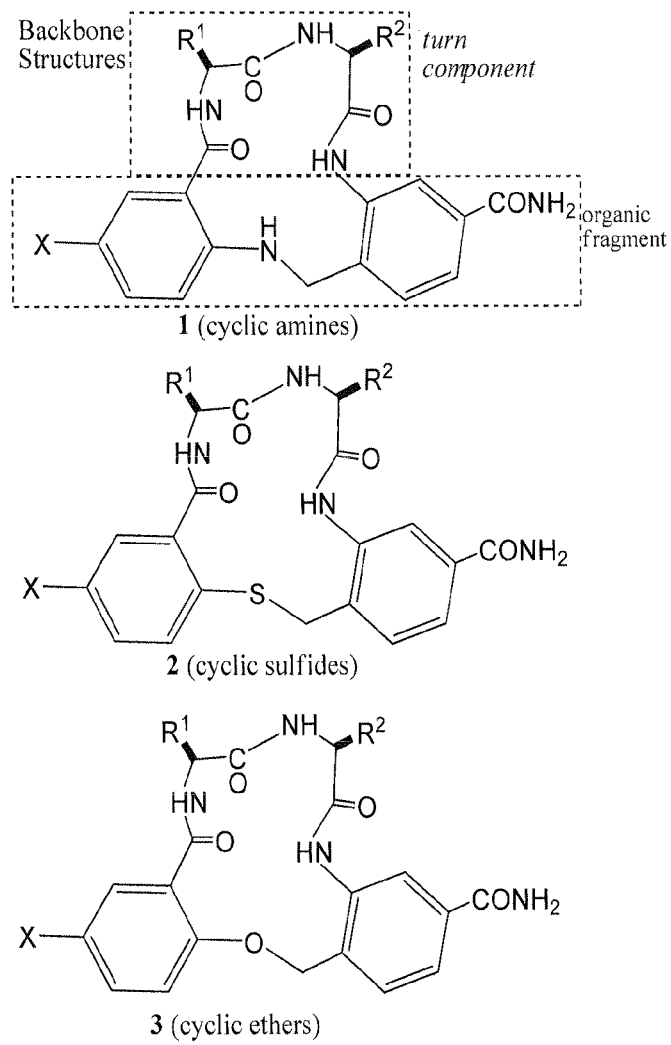
FIG 1B.
X-Substituents
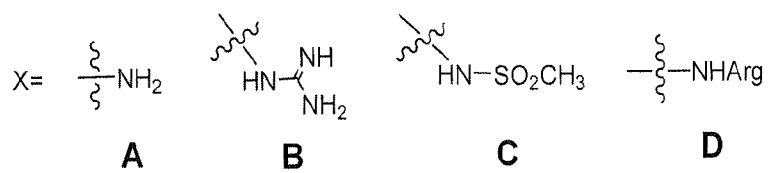
A  B  C  D
Dipeptide Fragments
FIG 1C.
| IK | NN | GK | EK | IR | TG |
|----|----|----|----|----|----|
| a  | b  | c  | d  | e  | f  |
| KG | IN | KT | EN | RG |
|----|----|----|----|----|
| g  | h  | i  | j  | k  |

D.

| Code | aa | Scaffold | X |
|---|---|---|---|
| 1Aa | IK | amine | amine |
| 1Ad | EK | amine | amine |
| 1Ba | IK | amine | guanidine |
| 3Aa | IK | ether | amine |
| 3Ac | GK | ether | amine |
| 3Ae | IR | ether | amine |
| 3Ak | RG | ether | amine |
| 3Ba | IK | ether | guanidine |
| 3Bg | KG | ether | guanidine |
| 3Bi | KT | ether | guanidine |
| 3Ca | IK | ether | methylsulfonamide |
| 3Ce | IR | ether | methylsulfonamide |
| 3Cg | KG | ether | methylsulfonamide |
| 3Ck | RG | ether | methylsulfonamide |

β-turn Peptidomimetic Cyclic

FIG. 1D

METHODS OF TREATING RETINITIS PIGMENTOSA

RELATED APPLICATION

This application is the U.S. National Stage of International Application No. PCT/US2010/025575, filed Feb. 26, 2010, which designates the U.S., published in English, and claims the benefit of U.S. Provisional Application No. 61/208,806, filed Feb. 27, 2009. The entire teachings of the above applications are incorporated herein by reference.

BACKGROUND OF THE INVENTION

Retinitis pigmentosa is a group of inherited disorders in which abnormalities of the photoreceptors (rods or cons) or the retinal pigment epithelium of the retina lead to progressive visual loss. Some forms of retinitis pigmentosa are dominant, requiring only one gene from either parent; others are X-linked, requiring only one gene from the mother. In some people, mostly males, an inherited form of hearing loss also develops.

The retinal pigment epithelium provides nutrients and support to the photoreceptor cells of the retina, in particular, inhibitors of oxidative stress and apoptosis. For example, neurotrophins of the retinal pigment epithelium activate the release of anti-inflammatory and anti-oxidative factors.

In retinitis pigmentosa there is chronic death of photoreceptor cells (rods and cones) of the retina. These photoreceptor cells, which are responsible for vision when light is low, gradually degenerate, so that vision becomes poor in the dark. The first symptoms of retinitis pigmentosa often begin in early childhood. Over time, a progressive loss of peripheral vision occurs. In the late stages of the disease, a person has a small area of central vision and a little peripheral vision remaining (tunnel vision). A need exists in the art for methods of treating retinitis pigmentosa.

SUMMARY OF THE INVENTION

The invention provides a method of treating retinitis pigmentosa in a subject in need thereof comprising administering to said subject an effective amount of a β-turn peptidomimetic cyclic compound. In one embodiment, the β-turn peptidomimetic cyclic compound comprises a macrocyclic ring of 13 to 17 carbon atoms. In a more particular embodiment, the β-turn peptidomimetic cyclic compound is represented by structural Formula (I):

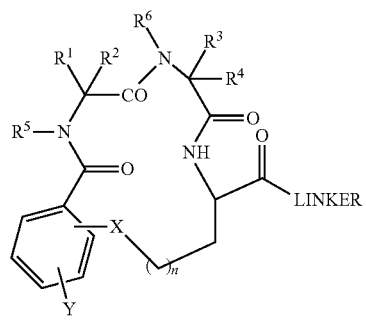

(I)

wherein $R^1$ and $R^3$ are independently selected from hydrogen, $C_1$ to $C_6$ alkyl, aryl or an amino acid side chain substituent found in the twenty protein-amino acids, in either enantiomeric configuration; $R^2$ and $R^4$ are independently hydrogen or $C_1$ to $C_6$ alkyl; or $R^1$ and $R^2$ together with the carbon atom to which they are attached form a cyclopropyl, cyclobutyl, cyclopentyl or cyclohexyl group; or $R^3$ and $R^4$ together with the carbon atom to which they are attached form a cyclopropyl, cyclobutyl, cyclopentyl or cyclohexyl group; $R^5$ and $R^6$ are hydrogen or $C_1$ to $C_6$ alkyl; Y is hydrogen or one or two aromatic substituents; X is selected from O, N, S, P, Se, C, alkylene of 1 to 6 carbon atoms, SO, $SO_2$ or NH; n is 0, 1, 2, 3, 4 or 5; and LINKER is a linking group effective to form dimers of the compound of formula (I) by reaction with a homo bifunctional compound. Suitable LINKER groups include, but are not limited to, $NH_2$, OH, SH, COOH, $CH_3CO$, CHO, and NH—$CH_2$—COOH.

In another embodiment of the present invention X is O, S or NH, $R^1$, $R^3$, $R^5$ and $R^6$ are each hydrogen atoms and the macrocyclic ring has 14, 15 or 16 ring atoms.

In another embodiment, $R^1$ and $R^3$ are derived from a sequence of different proteinogenic amino acids side chains.

In another embodiment of the present invention, X is O, S or NH.

In a particular embodiment, the β-turn peptidomimetic cyclic compound of Formula I is represented by the following Formula:

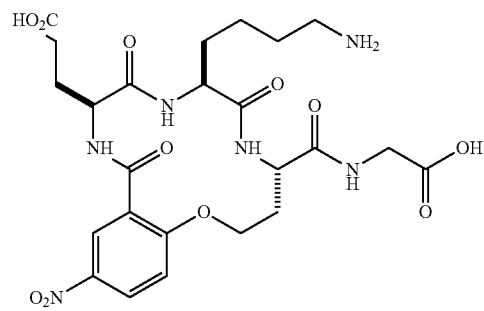

or a pharmaceutically acceptable salt thereof. The compound is referred to herein as D3. D3 has been demonstrated to possess Trk modulator activity.

In another embodiment, the β-turn cyclic compound is selected from the group consisting of:

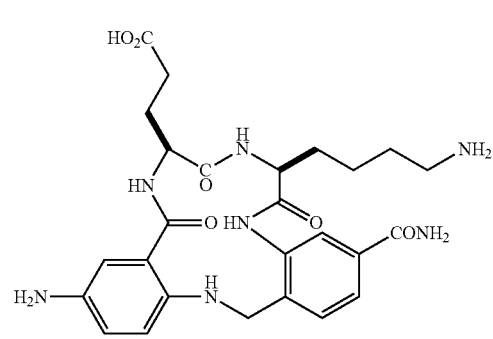

1Ad

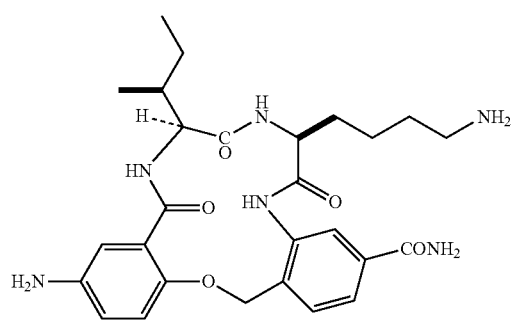
3Aa
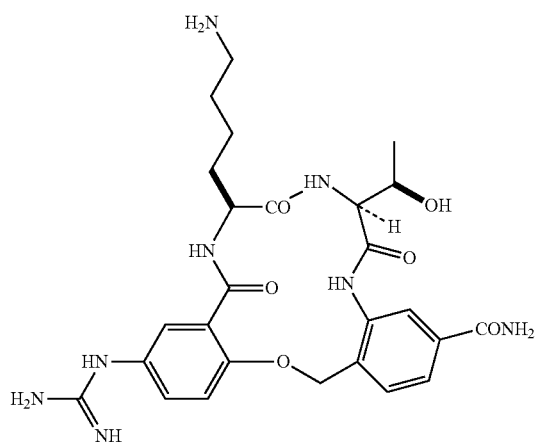
3Bi
3Ak
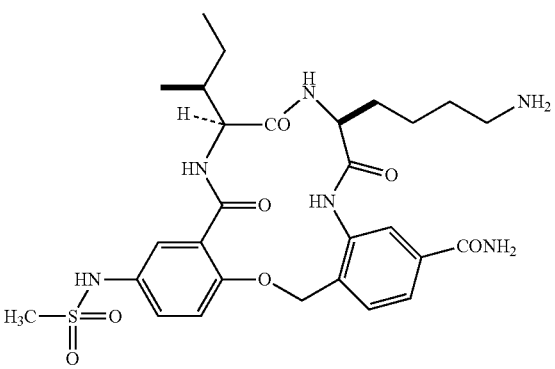
3Ca
3Ba
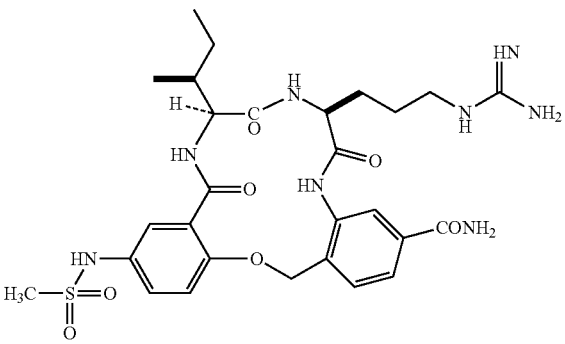
3Ce
3Bg

3Cg

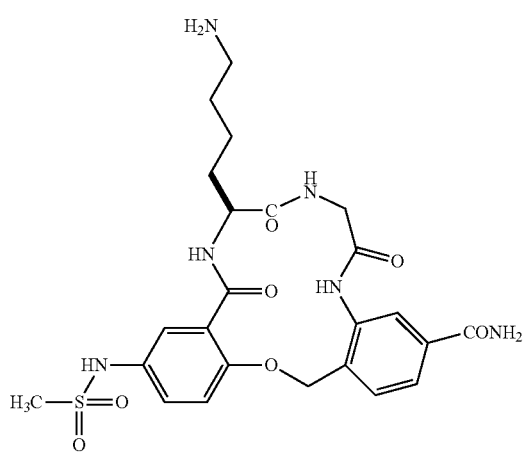

3Ck

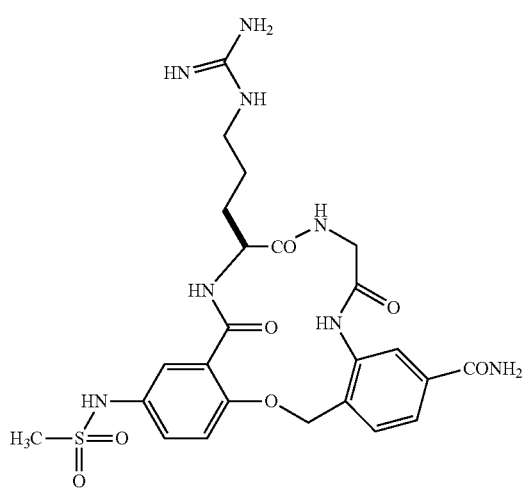

1Aa

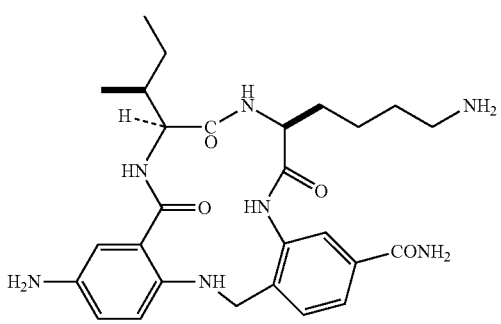

1Ba

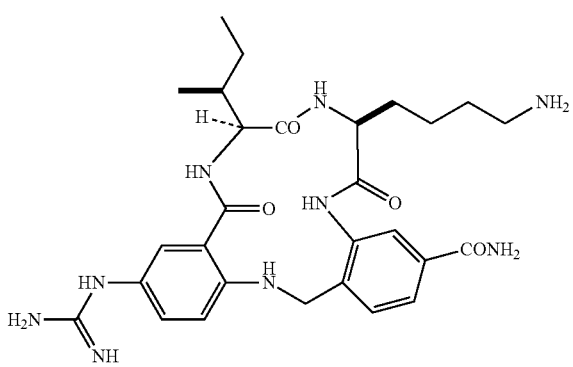

3Ac

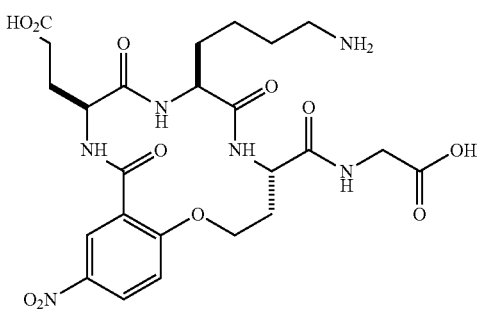

3Ae or a pharmaceutically acceptable salt of any of the foregoing. These compounds can possess Trk modulator activity.

In one embodiment, the invention relates to a method of treating retinitis pigmentosa in a subject in need thereof comprising administering to said subject an effective amount of a β-turn peptidomimetic cyclic compound represented by the following structural Formula (D3):

or a pharmaceutically acceptable salt thereof.

In another embodiment, the invention relates to a method of treating retinitis pigmentosa in a subject in need thereof comprising administering to said subject an effective amount of a β-turn peptidomimetic cyclic compound represented by Formula 3Aa:

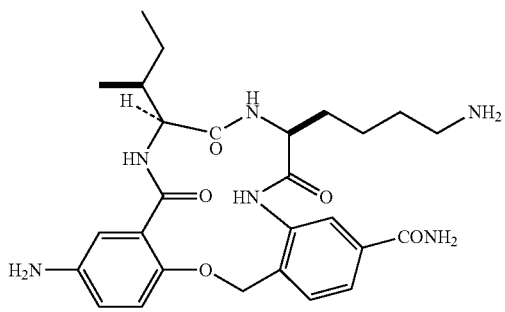

3Aa or a pharmaceutically acceptable salt thereof.

In yet another embodiment, the invention relates to a method of treating retinitis pigmentosa in a subject in need thereof comprising administering to said subject an effective amount of β-turn peptidomimetic cyclic compound represented by Formula 3Ak:

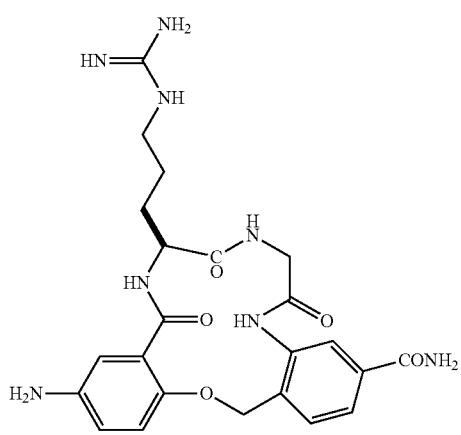

3Ak or a pharmaceutically acceptable salt thereof.

The invention further relates to the use of a compound described herein (e.g. a β-turn peptidomimetic cyclic compound) for the manufacture of a medicament for treating retinitis pigmentosa in a subject in need of treatment.

The invention further relates to a pharmaceutical composition useful for treating retinitis pigmentosa in a subject in need of treatment. The pharmaceutical composition comprises a compound described herein (e.g., β-turn peptidomimetic cyclic compound) and a pharmaceutically acceptable carrier.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

In the description of the Figures and the supporting experiments, the compound identifications include the prefix MIM. The compound identifications with the prefix are the same as the compound identifications absent the prefix. For example, MIM-D3 and D3 refer to the same compound.

FIG. 1A is the code for the β-turn backbones, numbered 1, 2 and 3, for Trk modulator compounds.

FIG. 1B is the code for X-substituents of the backbone, lettered A, B, C and D, for Trk modulator compounds.

FIG. 1C is the code for dipeptide $R^1$ and $R^2$ substituents of the backbone for Trk modulator compounds.

FIG. 1D illustrates the complete letter codes for β-turn peptidomimetic cyclic compounds including the backbone (1, 2 or 3), X-substituents (A, B, C or D) and dipeptide amino acids ($R^1$ and $R^2$).

DETAILED DESCRIPTION OF THE INVENTION

The present invention relates to methods of treating retinitis pigmentosa in a subject in need thereof comprising administering to said subject a β-turn peptidomimetic cyclic compound. As used herein, a "β-turn peptidomimetic cyclic compound" refers to cyclic compounds, which mimic the β-turn region of neurotrophin receptor ligands (e.g., NGF, NT-3, NT-4 and BDNF). In a particular embodiment, the β-turn peptidomimetic cyclic compound of the present invention can be a neurotrophin tyrosine kinase (Trk) receptor modulator. In another particular embodiment, the β-turn peptidomimetic cyclic compound can be a p75 receptor modulator. In yet another embodiment, the β-turn peptidomimetic cyclic compound can be both a p75 receptor modulator and a Trk receptor modulator.

In one embodiment, the β-turn peptidomimetic cyclic compound is represented by structural Formula I. In a particular embodiment, the β-turn peptidomimetic cyclic compound is compound D3 or derivatives of compound D3.

In another embodiment, the β-turn peptidomimetic cyclic compound can be a compound selected from the group consisting of: 1Ad, 3Aa, 3Ak, 3Ba, 3Bg, 3Bi, 3Ca, 3Ce, 3Cg, 3Ck, 1Aa, 1Ba, 3Ac and 3Ae.

Although the β-turn peptidomimetic cyclic compound of the present invention can be a Trk receptor modulator compound or a p75 receptor modulator, the usefulness of the β-turn peptidomimetic cyclic compound in treating retinitis pigmentosa can rely on other activities such as modulating the TrkB receptor or any other receptor whose modulation is useful in treating retinitis pigmentosa.

As used herein a "Trk receptor modulator compound" is a TrkA receptor agonist, TrkC receptor agonist, or a compound that is both a TrkA receptor agonist and a TrkC receptor agonist.

As used herein "modulating" or "modulator" refers to agonizing or antagonizing a receptor.

As used herein a "p75 receptor modulator" is a p75 receptor agonist or antagonist.

Neurotrophins and Neurotrophin Receptors

Neurotrophins (NTFs) are a family of dimeric proteins that regulate the proliferation, survival, and differentiation of neurons in all vertebrate species. The NTFs include Nerve Growth Factor (NGF), Brain Derived Neurotrophic Factor (BDNF), Neurotrophin-3 (NT-3) and Neurotrophin-4 (NT-4). These NTFs bind to two transmembrane receptors, the high affinity receptor family tyrosine kinase (Trk) (TrkA, Trk B and Trk C) ($K_d$=10-100 pM) and the p75 receptor ($K_d$=1 nM). The Trk family receptor ligands are quite selective (e.g., NGF binds TrkA, BDNF binds TrkB; and NT-3 binds mainly TrkC).

Neurotrophins and their receptors have been identified in conjunctival goblet cells (CGCs) (Rios, J. D., et al., "Role of Neurotrophins and Neurotrophin Receptors in Rat Conjunctival Goblet Cell Secretion and Proliferation, *Ophthalmology & Visual Science*, 48: 1543-1551 (2007)). CGCs are the primary source of large soluble mucins in the tear film. These mucins provide a physical and chemical barrier that protects the cornea and conjunctiva from exogenous agents (bacterial or chemical) and facilitates the occurrence of a smooth refractive surface necessary for clear vision.

β-Turn Peptidomimetic Cyclic Compounds

In one embodiment, the β-turn peptidomimetic cyclic compound comprises a macrocyclic ring of 13 to 17 carbon atoms. In a more particular embodiment, the β-turn peptidomimetic cyclic compound is represented by structural Formula (I):

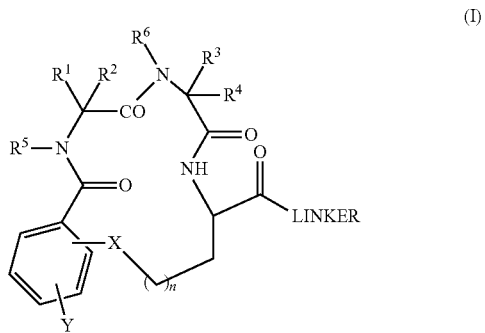

(I)

wherein $R^1$ and $R^3$ are independently selected from hydrogen, $C_1$ to $C_6$ alkyl, aryl or an amino acid side chain substituents found in the twenty protein-amino acids, in either enantiomeric configuration; $R^2$ and $R^4$ are independently hydrogen or $C_1$ to $C_6$ alkyl; or $R^1$ and $R^2$ together with the carbon atom to which they are attached form a cyclopropyl, cyclobutyl, cyclopentyl or cyclohexyl group; or $R^3$ and $R^4$ together with the carbon atom to which they are attached form a cyclopropyl, cyclobutyl, cyclopentyl or cyclohexyl group; $R^5$ and $R^6$ are hydrogen or $C_1$ to $C_6$ alkyl; Y is hydrogen or one or two aromatic substituents; X is selected from O, N, S, P, Se, C, alkylene of 1 to 6 carbon atoms, SO, $SO_2$ or NH; n is 0, 1, 2, 3, 4 or 5; and LINKER is a linking group effective to form dimers of the compound of formula (I) by reaction with a homo bifunctional compound. Suitable LINKER groups include, but are not limited to, $NH_2$, OH, SH, COOH, $CH_3CO$, CHO, and NH—$CH_2$—COOH.

The twenty amino-acid side chain substituents include the side chains of alanine, cysteine, aspartic acid, glutamic acid, phenylanine, glycine, histidine, isoleucine, lysine, leucine, methionine, asparagine, proline, glutamine, arginine, serine, threonine, valine, tryptophan, and tyrosine. For example, the side chain of glutamic acid is

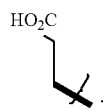

In another embodiment of the present invention X is O, S or NH, $R^1$, $R^3$, $R^5$ and $R^6$ are each hydrogen atoms and the macrocyclic ring has 14, 15 or 16 ring atoms.

In another embodiment, $R^1$ and $R^3$ are derived from a sequence of different protein amino acids side chains.

In another embodiment of the present invention, X is O, S or NH.

In a particular embodiment, the β-turn peptidomimetic cyclic compound is D3 (see Maliartchouk et al., *Mol Pharmcol* 57(2):385-391, 2000, which is incorporated herein by reference in its entirely and U.S. Pat. No. 6,881,719, which is incorporated herein by reference in its entirely), or derivatives of D3. A number of derivatives of D3 and other compounds of Formula I are envisioned for use in the methods of the invention and include simple modifications like biotinylated forms and molecules wherein two such units are linked by dimers. Other derivatives of D3 and other compounds of Formula I include side chains $R^1$-$R^6$ having amino acid side chain substituents found in the twenty protein-amino acids.

The side chains typical of the protein amino acids (e.g., Arg, Trp, His) allow for the formation/design of a diversity of structures that are easily generated derivatives of D3 and other compounds of Formula I, and they can include many types of functional groups.

The substituent(s) Y may be hydrogen or one or two aromatic substituents for example nitro, amino, halo, alkyl for example alkyl of 1 to 6, preferably 1 to 4 carbon atoms, and aryl for example phenyl or naphthyl. The alkyl and aryl substituents Y may be unsubstituted or substituted, suitable substituents being nitro and alkyl of 1 to 6 carbon atoms. Y may also be derivatized with a functional group, for example biotin. The group X may be any nucleophilic atom like O, N, S, P, Se, but also others such as C, or may be an alkylene radical typically of 1 to 6 carbon atoms, for example methylene; SO, $SO_2$ or NH. The point of connection could be ortho- or meta- to the benzoyl carbonyl. Permissible values of "n" are 0, 1, 2, 3, 4, and 5. The linking side chain that incorporates X is aliphatic as indicated in structure (I).

The side chain alkyl groups $R^1$, $R^2$, $R^3$, $R^4$, $R^5$, and $R^6$ can be varied in many ways to enhance the biological activities of these compounds. Typically $R^1$, $R^2$, $R^3$, and $R^4$ are amino acid side-chain substituents found in the twenty protein-amino acids, for example the side-chains of glutamic acid, lysine, ornithine and threonine, in either enantiomeric configuration. If the $R^1$ substituent is an amino acid side chain, the other substituent on that carbon, $R^2$, will typically be hydrogen, but could also be methyl, ethyl or benzyl. Alternatively, $R^1$ and $R^2$ together with their intervening atoms can be joined to give cyclopropane, cyclobutane, cyclopentane, and cyclohexane, residues. $R^3$ and $R^4$ are related in the same way as $R^1$ and $R^2$ as described above. That is, one of them will be an amino acid side chain with the other of these two substituents being hydrogen in most cases, but could also be methyl, ethyl, propyl or benzyl. In addition, $R^3$ and $R^4$ together with the intervening atoms can be joined to give cyclopropane, cyclobutane, cyclopentane, and cyclohexane, residues.

There is much scope for variation in $R^5$ and $R^6$ with the most common substituent at these positions being hydrogen or methyl. Those substituents can also be designed to correspond to one of the side chains of the twenty protein-amino acids, in particular, methyl.

Side chains found to be particularly conducive to biological activities are $R^1$ and $R^3$ as side chains of lysine, glutamic acid, tyrosine, iso-leucine, asparagine, and threonine, $R^2$, $R^4$, $R^5$, and $R^6$ as hydrogen. One or more of the side chains are selected especially to correspond to side chains within the turn regions of NGF.

In general, the macrocyclic compounds have 13 to 16 membered rings where the X substituent is O, N, S, SO, or $SO_2$.

In another embodiment, the β-turn peptidomimetic cyclic compound is selected from the group consisting of: 1Ad, 3Aa, 3Ak, 3Ba, 3Bg, 3Bi, 3Ca, 3Ce, 3Cg, 3Ck, 1Aa, 1Ba, 3Ac and 3Ae.

In yet another embodiment, the β-turn peptidomimetic cyclic compound is a compound comprising a cyclic amino, ether or sulfide scaffold (see FIG. 1A), with various substituents (e.g., amine, guanidine or methylsulfonamide) (see FIG. 1B) and $R^1$ and $R^2$ groups comprising dipeptide amino acid fragments (see FIG. 1C). (See also FIG. 1D).

The compound of the present invention is present in an effective amount. As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

As used herein, "retinitis pigmentosa" is a wide concept which is intended to include, but is not limited to, Usher syndrome, Leber's congenital amaurosis, rod-cone disease, Bardet-Biedl syndrome, Refsum disease, Stargardt's disease, choroideremia, gyrate-atrophy, Laurence-Moon syndrome, Warrdenburg syndrome, Alport syndrome, Kearns-Sayre syndrome, abetalipoproteinemia, Hurler syndrome, Scheie syndrome, Sanfilippo syndrome, neuronal ceroid lipofuscinosis, Kufs syndrome, Jansky-Bielschowsky disease, Vogt-Spielmeyer-Batten disease and muscular dystrophy.

Subject, as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species. In one embodiment, the subject is a human.

The term "treating" includes both therapeutic treatment and prophylactic treatment (reducing the likelihood of development). The term means decrease, suppress, attenuate, diminish, arrest, or stabilize the development or progression of a disease (e.g., a disease or disorder delineated herein), lessen the severity of the disease or improve the symptoms associated with the disease.

As used herein, the term pharmaceutically acceptable salt refers to a salt of the administered compounds prepared from pharmaceutically acceptable non-toxic acids including inorganic acids and organic acids thereof. Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

The invention further relates to pharmaceutical compositions for use in treating retinitis pigmentosa in a subject in need of treatment. The pharmaceutical composition comprises one or more β-turn peptidomimetic cyclic compounds of the present invention and a pharmaceutically acceptable carrier. Pharmaceutically acceptable carriers can also contain inert ingredients which do not interact with the regulatory/active substances in the compositions. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate, dextrose, ethanol, surfactants such as glycerol, or excipients.

In a further embodiment, the pharmaceutical composition further comprises an (i.e., one or more) additional therapeutic agent. An additional therapeutic agent suitable for use in the methods and pharmaceutical compositions described herein, can be, but is not limited to, for example vitamin A (e.g., vitamin A palmitate), bendazac, NT-501 (Neurotech), and human postpartum umbilical cord cells.

Modes of Administration

The composition can be formulated for topical ophthalmic application, for example, in the form of solutions, ointments, creams, lotions, eye ointments and, most preferably, eye drops or eye gels and can contain the appropriate conventional additives, including, for example, preservatives, solvents to assist drug penetration, and emollients in ointments and creams. Such topical formulations can contain compatible conventional carriers, for example cream or ointment bases, and ethanol or oleyl alcohol for lotions.

Alternatively, the active compounds may be applied to the eye via liposomes. Further, the active compounds may be infused into the tear film via a pump-catheter system. Another embodiment of the present invention involves the active compound contained within a 20 continuous or selective-release device, for example, membranes such as, but not limited to, those employed in the pilocarpine (OCUSERT™) System (Alza Corp., Palo Alto, Calif.). As an additional embodiment, the active compounds can be contained within, carried by, or attached to contact lenses which are placed on the eye. Another embodiment of the present invention involves the active compound contained within a swab or sponge which can be applied to the 25 ocular surface. Another embodiment of the present invention involves the active compound contained within a liquid spray which can be applied to the ocular surface. Another embodiment of the present invention involves an injection of the active compound directly into the eye.

When the pharmaceutical composition of the present invention for treating retinitis pigmentosa is used as an ophthalmic solution, it is provided in any dosage form which is used for ophthalmic solution, for example, an aqueous eye drop such as aqueous ophthalmic solution, aqueous suspended ophthalmic solution, viscous ophthalmic solution and solubilized ophthalmic solution, or a non-aqueous ophthalmic solution such as non-aqueous ophthalmic solution and non-aqueous suspended ophthalmic solution. Among these, the aqueous ophthalmic solution is preferable.

When the pharmaceutical composition of the present invention for treating retinitis pigmentosa is prepared into an aqueous ophthalmic solution, various additives normally used in the aqueous ophthalmic solution are conveniently contained therein as long as the object of the present invention is not adversely affected. Examples of such the additives include buffers, isotonizing agents, preservatives, solubilizers (stabilizers), pH adjusting agents, thickeners and chelating agents.

The buffers may be selected from but not limited by the group comprising a phosphate buffer, a borate buffer, a citrate buffer, a tartrate buffer, an acetate buffer (for example, sodium acetate) and an amino acid.

The isotonizing agents may be selected from but not limited by the group comprising sugars such as sorbitol, glucose and mannitol, polyhydric alcohols such as glycerin, polyethylene glycol and polypropylene glycol, and salts such as sodium chloride.

The preservatives may be selected from but not limited by the group comprising benzalkonium chloride, benzethonium chloride, alkyl paraoxybenzoates such as methyl paraoxybenzoate and ethyl paraoxybenzoate, benzyl alcohol, phenethyl alcohol, sorbic acid and salts thereof, thimerosal and chlorobutanol.

The solubilizers (stabilizers) may be selected from but not limited by the group comprising cyclodextrin and derivatives thereof, water-soluble polymers such as poly(vinylpyrrolidone), and surfactants such as polysorbate 80 (trade name: Tween 80).

The pH adjusting agents may be selected from but not limited by the group comprising hydrochloric acid, acetic acid, phosphoric acid, sodium hydroxide, potassium hydroxide and ammonium hydroxide.

The thickeners may be selected from but not limited by the group comprising hydroxyethylcellulose, hydroxypropylcellulose, methylcellulose, hydroxypropylmethylcellulose and carboxymethylcellulose and salts thereof.

The chelating agents may be selected from but not limited by the group comprising sodium edetate, sodium citrate and sodium condensed phosphate.

When the pharmaceutical composition of the present invention for treating retinitis pigmentosa is prepared into an ophthalmic ointment, a base compound must be present. The base of the ophthalmic ointment may be selected from but not limited by the group comprising purified lanolin, VASELINE®, plastibase, liquid paraffin and polyethylene glycol.

Alternatively, the composition of the invention can be formulated for oral administration using pharmaceutically acceptable tableting excipients including lactose, microcrystalline cellulose, corn starch, stearic acid, or the like, can be used. Oral administration can also comprise a liquid composition formulated in water, glycols, oils, alcohols or the like.

Coadministration

When the methods of the invention include coadministration, coadministration refers to administration of a first amount of a β-turn peptidomimetic cyclic compound or a pharmaceutically acceptable salt thereof and a second amount of at least one agent selected from the group consisting of vitamin A (e.g., vitamin A palmitate), bendazac, NT-501 (Neurotech), and human postpartum umbilical cord cells, wherein the first and second amounts together comprise an effective amount to treat retinitis pigmentosa in a subject in need of treatment. Coadministration encompasses administration of the first and second amounts of the coadministration in an essentially simultaneous manner, such as in a single pharmaceutical composition, or in multiple pharmaceutical compositions. In addition, such coadministration also encompasses use of each compound in a sequential manner in either order. When coadministration involves the separate administration of the first amount of the β-turn peptidomimetic cyclic compound or a pharmaceutically acceptable salt thereof and a second amount of at least one agent selected from the group consisting of vitamin A (e.g., vitamin A palmitate), bendazac, NT-501 (Neurotech), and human postpartum umbilical cord cells, the agents are administered sufficiently close in time to have the desired therapeutic effect. For example, the period of time between each administration which can result in the desired therapeutic effect, can range from minutes to hours and can be determined taking into account the properties of each component of the coadministration, such as potency, solubility, bioavailability, plasma half-life and kinetic profile.

Dosing

An effective amount of a β-turn peptidomimetic cyclic compound will depend on the age, sex and weight of the patient, the current medical condition of the patient and the nature of the retinitis pigmentosa being treated. The skilled artisan will be able to determine appropriate dosages depending on these and other factors. For example, when the pharmaceutical composition of the present invention is used as an ophthalmic solution for treating retinitis pigmentosa, in a subject in need thereof, it is desirable that an aqueous solution eye drop contain an active ingredient of a compound of the present invention in an amount of approximately 0.001 to 2.5 (w/v) %, such as from 0.02 to 2.0 (w/v), for example from about 0.03 to 1.5 (w/v) %, for example from about 0.05 to 1.0 (w/v) %. As used herein, weight/volume (w/v) means specific mass of solute in a specific final volume (e.g., g/ml). When administered, the compounds and compositions of this invention can be given once daily or with multiple daily doses such as twice per day, three times per day and four times per day. In a particularly preferred embodiment, the compound and compositions of the present invention can be given in a dose of one to five drops, for example, one drop, two drops, three drops, four drops or five drops.

When the pharmaceutical composition of the present invention is used as an ocular ointment, it is desirable that an ocular ointment contain an active ingredient of a compound of the present invention in an amount of approximately 0.001 to 2.5 (w/w) %, such as from 0.02 to 2.0 (w/v), for example from about 0.03 to 1.5 (w/v) %, for example from about 0.05 to 1.0 (w/v) %. As used herein, weight/weight (w/w) means weight of solute in final weight of the solution, e.g., g/g. When administered, the compounds and compositions of this invention maybe given once daily or with multiple daily doses such as twice per day, three times per day and four times per day.

A description of example embodiments of the invention follows.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

Exemplification

Neurotrophic Protection of Retinal Pigmented Epithelial Cells from Degeneration Due to Oxidative Stress The purpose of this study was to investigate the pharmacological concept of neurotrophic prevention of oxidative-stress-induced degeneration of retinal pigmented epithelial (RPE) cells. The aim of this study was to validate specific compounds as therapy for retinitis pigmentosa.

Methods

APRE19 cells were cultured in complete media, followed by eight hours of serum starvation. Then apoptosis was induced by exposure to oxidative stress (TNFα and $H_2O_2$), in the presence or absence of test compounds or controls for sixteen hours. Apoptosis was quantified as the percentage of dead cells over total live+dead cells by counting nuclei stained with Hoechst reagent.

Test agents included nerve growth factor (an agonist of TrkA and p75 receptors), Neurotrophin-3 (an agonist of TrkC and p75 receptors), and compounds D3, 3Ak, 3Ae and 3Aa.

Results

Non-stressed cells are fully viable, however, oxidative stress results in the apoptotic death of 94% of the APRE19 cells. Protection of stressed APRE19 cells by neurotrophins NGF or NT-3 has been published.

Compounds D3, 3Ak and 3Ae afford a quantitative and significant protection of apoptosis, in a dose dependent manner. Treatment with compounds D3, 3Ak and 3Ae result in lower APRE19 cells death (29%, 24%, and 16% respectively, at 25 μM doses).

Compound 3Aa affords a quantitative and significant protection of apoptosis. However, protection is not dose dependent and is less than that seen with compounds D3, 3Ak and 3Ae. Treatment with compound 3Aa, at 25 μM doses, is partially protective and results in 50% APRE19 cell death.

Compounds D3, 3Ak, 3Ae and 3Aa can protect RPE cells from death. Treatment with Compounds D3, 3Ak and 3Ae resulted in cell death less than 30%, whereas 3Aa resulted in cell death of about 50%. These compounds are potential therapy for retinitis pigmentosa.

Additional experiments in a mouse model of retinal degeneration were conducted. Compound 3Aa was administered and ERG (scotopic and photopic) and the number of Outer Nuclear Layer rows was observed for both control treated and drug treated animals. Although results did not show a drug effect that was statistically significant from control, positive trends in the data were observed.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating retinitis pigmentosa in a subject in need thereof comprising administering to said subject an effective amount of a β-turn peptidomimetic cyclic compound, wherein said β-turn peptidomimetic cyclic compound is represented by structural Formula (I):

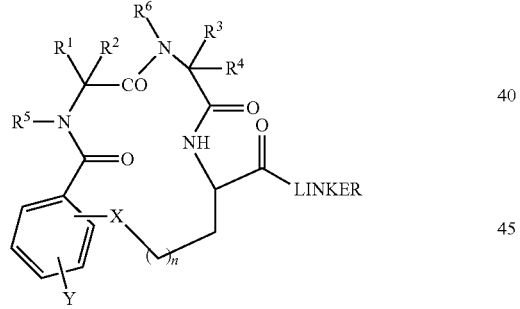

(I)

wherein $R^1$ and $R^3$ are independently selected from hydrogen, $C_1$ to $C_6$ alkyl, aryl, or amino acid side chain substituent found in the twenty protein-amino acids; $R^2$ and $R^4$ are independently hydrogen or alkyl; or $R^1$ and $R^2$ together with the carbon atom to which they are attached form a cyclopropyl, cyclobutyl, cyclopentyl or cyclohexyl group; or $R^3$ and $R^4$ together with the carbon atom to which they are attached form a cyclopropyl, cyclobutyl, cyclopentyl or cyclohexyl group; $R^5$ and $R^6$ are hydrogen or $C_1$ to $C_6$ alkyl; Y is hydrogen or one or two aromatic substituents; X is selected from O, N, S, P, Se, C, alkylene of 1 to 6 carbon atoms, SO, $SO_2$ or NH; n is 0, 1, 2, 3, 4 or 5; and LINKER selected from the group consisting of: $NH_2$, OH, SH, COOH, $CH_3CO$, CHO, and $NH$—$CH_2$—COOH.

2. The method of claim 1, wherein X is O, S or NH, $R^1$, $R^3$, $R^5$ and $R^6$ are each hydrogen atoms and the macrocyclic ring has 14, 15 or 16 ring atoms.

3. The method of claim 1, wherein $R^1$ and $R^3$ are derived from a sequence of different amino acids side chains.

4. The method of claim 3, wherein X is O, S or NH.

5. The method of claim 1, wherein said β-turn peptidomimetic cyclic compound is selected from the group consisting of:

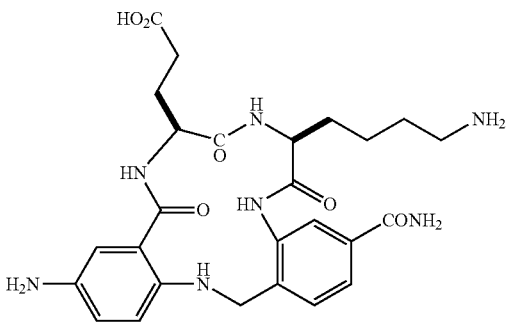

1Ad

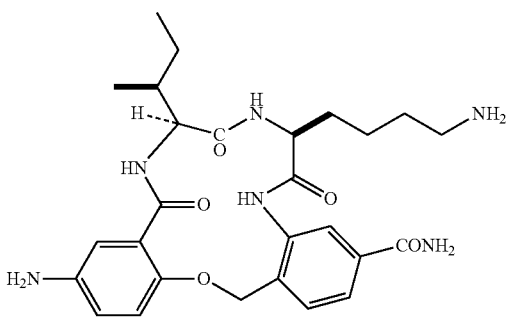

3Aa

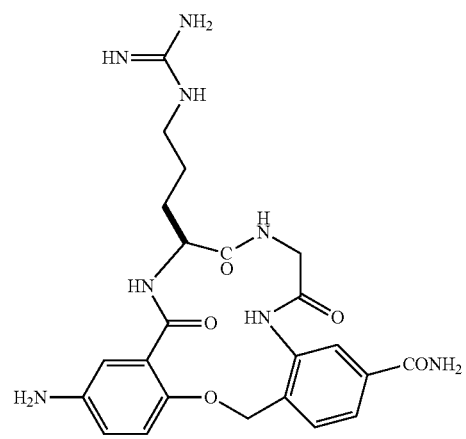

3Ak

3Ba
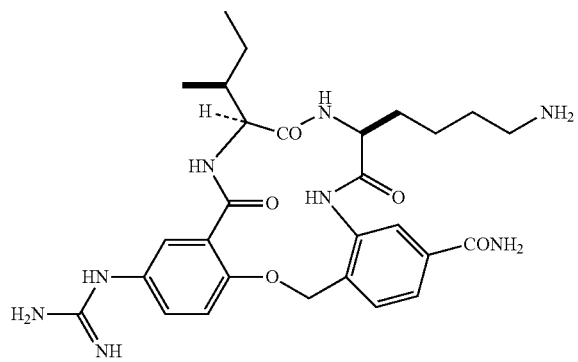
3Bg
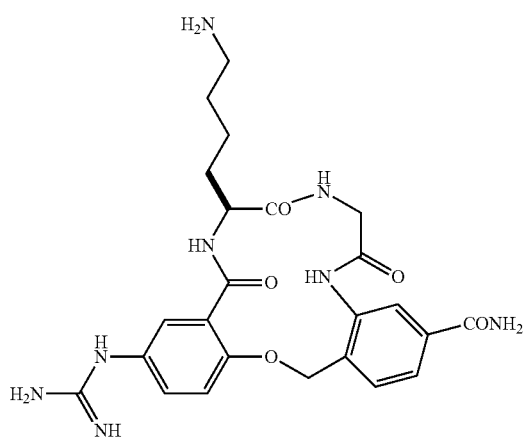
3Bi
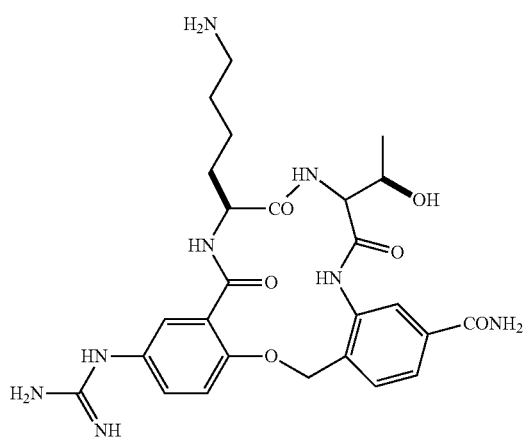
3Ca
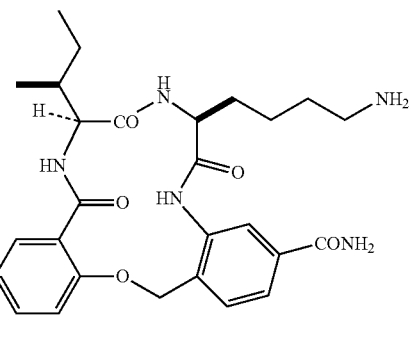
3Ce
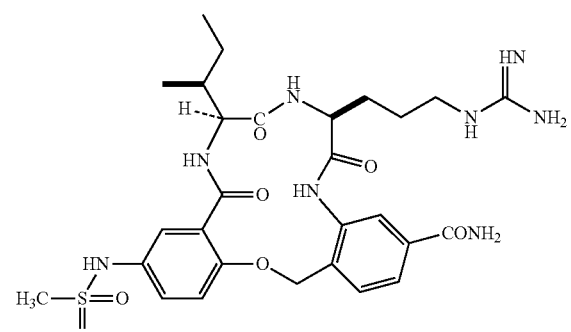
3Cg
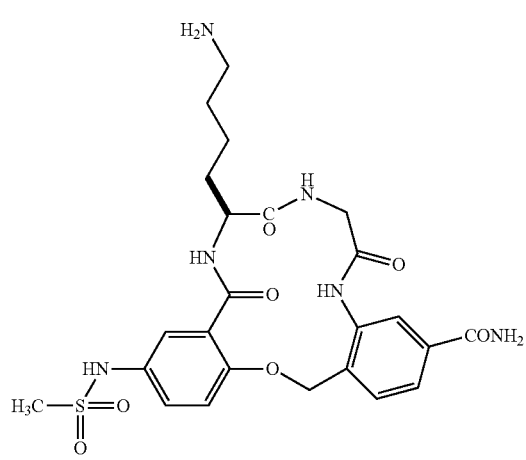

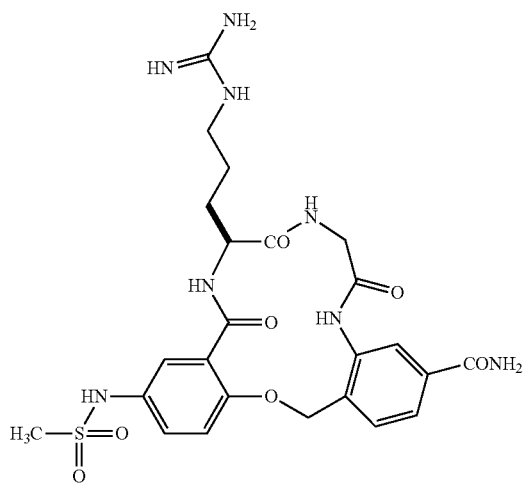

3Ck

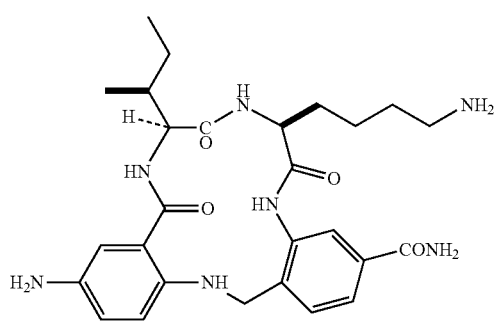

1Aa

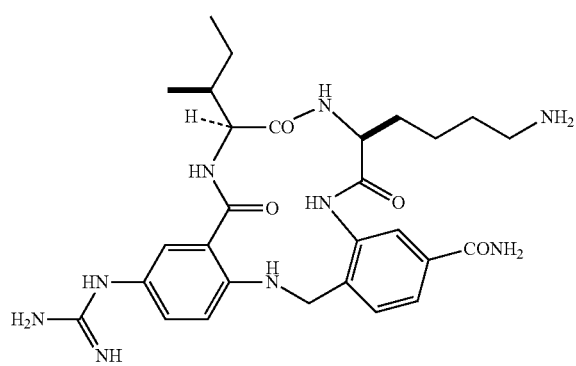

3Ac

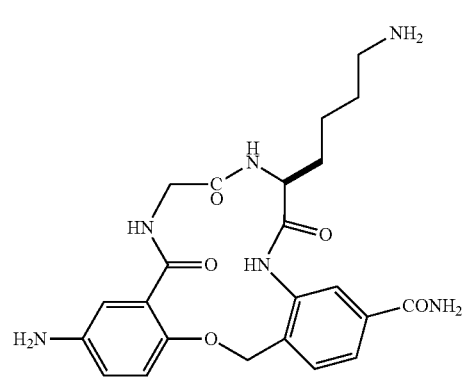

and

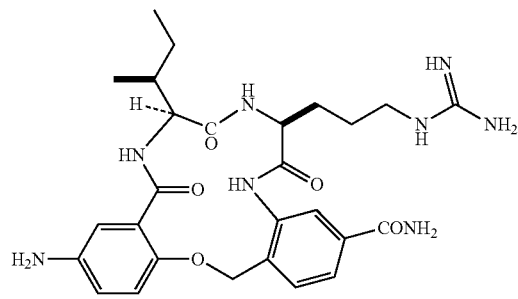

3Ae or a pharmaceutically acceptable salt thereof.

6. A method of treating retinitis pigmentosa in a subject in need thereof comprising administering to said subject an effective amount of a β-turn peptidomimetic cyclic compound represented by Formula D3:

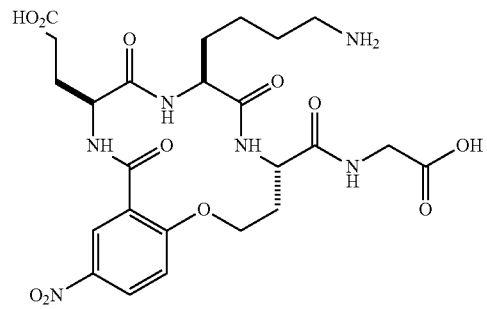

1Ba or a pharmaceutically acceptable salt thereof.

7. A method of treating retinitis pigmentosa in a subject in need thereof comprising administering to said subject an effective amount of a β-turn peptidomimetic cyclic compound represented by Formula 3Ae:

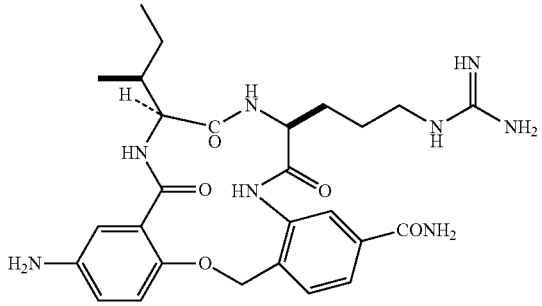

3Ae or a pharmaceutically acceptable salt thereof.

8. A method of treating retinitis pigmentosa in a subject in need thereof comprising administering to said subject an effective amount of a β-turn peptidomimetic cyclic compound represented by Formula 3Ak:

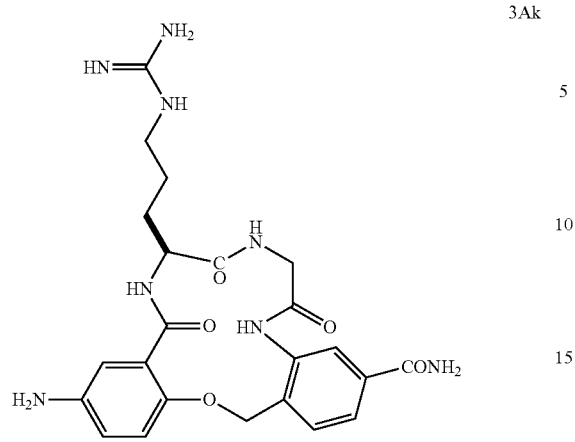
or a pharmaceutically acceptable salt thereof.
* * * * *